(12) United States Patent
Pethö et al.

(10) Patent No.: US 7,951,798 B2
(45) Date of Patent: May 31, 2011

(54) POLYMORPHS OF OLANZAPINE HYDROCHLORIDE

(75) Inventors: János Pethö, Budapest (HU); József Barkóczy, Budapest (HU); Péter Kótay Nagy, Vác (HU); Gyula Simig, Budapest (HU); Zsuzsa Szent-Királlyi, Budapest (HU)

(73) Assignee: Egis Hyogyszergyar Nyrt., Budapest (HU)

( * ) Notice: Subject to any disclaimer, the term of this patent is extended or adjusted under 35 U.S.C. 154(b) by 1048 days.

(21) Appl. No.: 10/553,908

(22) PCT Filed: Apr. 22, 2004

(86) PCT No.: PCT/HU2004/000042
§ 371 (c)(1),
(2), (4) Date: Sep. 11, 2006

(87) PCT Pub. No.: WO2004/094433
PCT Pub. Date: Nov. 4, 2004

(65) Prior Publication Data
US 2007/0004706 A1    Jan. 4, 2007

(30) Foreign Application Priority Data
Apr. 22, 2003  (HU) .................................. 0301082

(51) Int. Cl.
*A61P 25/18* (2006.01)
*A61K 31/551* (2006.01)
*C07D 495/04* (2006.01)

(52) U.S. Cl. ........................................ 514/220; 540/557
(58) Field of Classification Search .................. 514/220; 540/557
See application file for complete search history.

(56) References Cited

U.S. PATENT DOCUMENTS
5,229,382 A * 7/1993 Chakrabarti et al. .......... 514/220
7,459,449 B2 * 12/2008 Keltjens ........................ 514/220

FOREIGN PATENT DOCUMENTS
EP     0 454 436 A     10/1991
WO    WO-00/18408 A    4/2000
WO    WO-03/007912 A   1/2003

* cited by examiner

*Primary Examiner* — Brenda L Coleman
(74) *Attorney, Agent, or Firm* — Birch, Stewart, Kolasch & Birch, LLP

(57) ABSTRACT

The present invention relates to new crystalline forms I, II and III of 2-methyl-4-(4-methylpiperazin-1-yl)-10H-thieno[2,3-b][1,5]-benzodiazepine hydrochloride, a process for the preparation thereof and pharmaceutical compositions containing the same. Said new polymorphic forms are useful as active ingredients for the treatment of psychotic conditions.

21 Claims, 3 Drawing Sheets

POLYMORPHS OF OLANZAPINE HYDROCHLORIDE

This application is a national stage entry under 35 U.S.C. §371 of PCT/HU04/00042, filed Apr. 22, 2004.

TECHNICAL FIELD OF THE INVENTION

The present invention relates to new polymorphic hydrochloride salts of olanzapine, a process for the preparation thereof, pharmaceutical compositions containing said new polymorphic hydrochloride salts and the use of said salts for the treatment of psychotic conditions.

More particularly the present invention is concerned with new crystalline forms of the hydrochloride salts of 2-methyl-4-(4-methylpiperazin-1-yl)-10H-thieno-[2,3-b][1,5]-benzodiazepine (olanzapine),

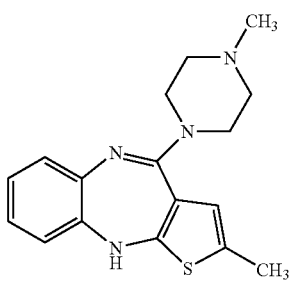

a process for the preparation thereof, pharmaceutical compositions containing the same and the use of said polymorphic hydrochloride salts for the treatment of psychotic conditions.

TECHNICAL BACKGROUND

It is known that 2-methyl-4-(4-methylpiperazin-1-yl)-10H-thieno[2,3-b]-[1,5]-benzodiazepine, also known as olanzapine (INN), is a drug widely used for the treatment of psychotic conditions.

Olanzapine as a base was described the first time in EP No. 454,436. In the specification a great number of inorganic and organic acids are mentioned as acids that can be used for salt formation, including hydrochloric acid. However, only the preparation of the olanzapine base is exemplified, no salt of olanzapine is characterized by physical-chemical parameters (e.g. melting point), and no process is disclosed for the preparation of any salt. Said patent specification is completely silent in mentioning any crystal form of the olanzapine base. There is not even a hint in the specification at the crystalline form of olanzapine base.

European Patent No. 733,635 discloses and claims polymorph form II olanzapine base. According to this specification olanzapine base prepared as specified in EP 454,436 is unstable, unsuitable for the preparation of pharmaceutical formulations and thus cannot be put on the market. According to this document the new olanzapine base of crystalline form II is sufficiently stable. Olanzapine base prepared as specified in EP 454,436 is designated as polymorph I.

Crystalline modifications of olanzapine base formed with one mole of methanol, one mole of ethanol and one mole of 1-propanol are disclosed and claimed in European Patent No. 733,634. This document is concerned with the crystalline monomethanol, monoethanol and mono-1-propanol solvates of olanzapine. The advantage of these crystalline solvates over the olanzapine base prepared according to EP 454,436 resides in the fact that by using methanol, ethanol or 1-propanol the product can be prepared in much higher purity, and only a single recrystallization is necessary during the purification.

Polymorph forms III, IV and V of olanzapine are described and claimed in WO 01/47933. These forms are prepared by dissolving olanzapine base in a mixture of acetic acid, formic acid or hydrochloric acid and water, neutralizing the acidic solution with ammonium hydroxide or sodium hydroxide and isolating the separating polymorph. According to the specification the advantage of polymorph forms III, IV and V of olanzapine is that during the reaction carried out in a medium free of solvent a solvate-free product containing only a negligible amount of residual solvent can be obtained.

European Patent No. 831,098 discloses and claims crystalline modifications B, D and E of olanzapine dihydrate. According to the specification olanzapine dihydrates prepared in aqueous medium are intermediates of the polymorph form II olanzapine provided in EP No. 733,635, which can be converted into polymorph form II olanzapine by vacuum drying carried out at a temperature between 40° C. and 70° C. The advantage of this process is that the anhydrous polymorphic crystalline form II, which is considered to be the most stable crystalline form, can be prepared via olanzapine dihydrate intermediate in an environmentally advantageous manner.

Crystalline modifications of olanzapine formed with dichloromethane are described and claimed in U.S. Pat. No. 5,637,584. According to this document olanzapine can be present in two anhydrous polymorphic forms. One of them, the polymorph designated as form II is metastable, consequently unsuitable for the preparation of pharmaceutical preparations, while the polymorph designated as form I is stable and suitable for pharmaceutical use in every respect. According to the specification the solvate of olanzapine formed with dichloromethane can be used for the preparation of anhydrous polymorphic form I olanzapine.

From the above references it is apparent that the production of anhydrous and stable olanzapine encounters serious difficulties. Olanzapine base forms solvates readily with water or solvents, consequently the preparation of crystalline olanzapine suitable for pharmaceutical use with regard to the residual solvent content is problematical.

SUMMARY OF THE INVENTION

It is the object of the present invention to develop a new form of olanzapine which has favourable properties for the preparation of pharmaceutical compositions meeting the requirements of the pharmaceutical industry.

The above object is solved by the present invention.

The present invention is based on the recognition that olanzapine hydrochloride can be prepared in three different, morphologically homogeneous crystalline forms. While polymorphic forms I and II contain two molar equivalents of hydrochloric acid, polymorphic form III contains one molar equivalent of hydrochloric acid.

Analytical studies revealed that the solubility of olanzapine base in water is significantly lower than that of the new polymorphic salts prepared according to the present invention.

There is a strong demand in the pharmaceutical industry for stable and morphologically uniform active ingredients of high purity, namely these requirements are fundamental conditions for complying the requirements towards medicines. Morphologically homogeneous products have other advantages from technological point of view, too. They enable the manufacture of products with constant filtration and drying characteristics. Scaling up of morphologically uniform products can be performed reproducibly. A further advantage of morphologically homogeneous products resides in that they can be stored for a long period without applying specific conditions.

The new hydrochloride salts of 2-methyl-4-(4-methylpiperazin-1-yl)-10H-thieno-[2,3-b][1,5]-benzodiazepine according to the present invention comply with these requirements.

DETAILS OF THE INVENTION

Figure 1:
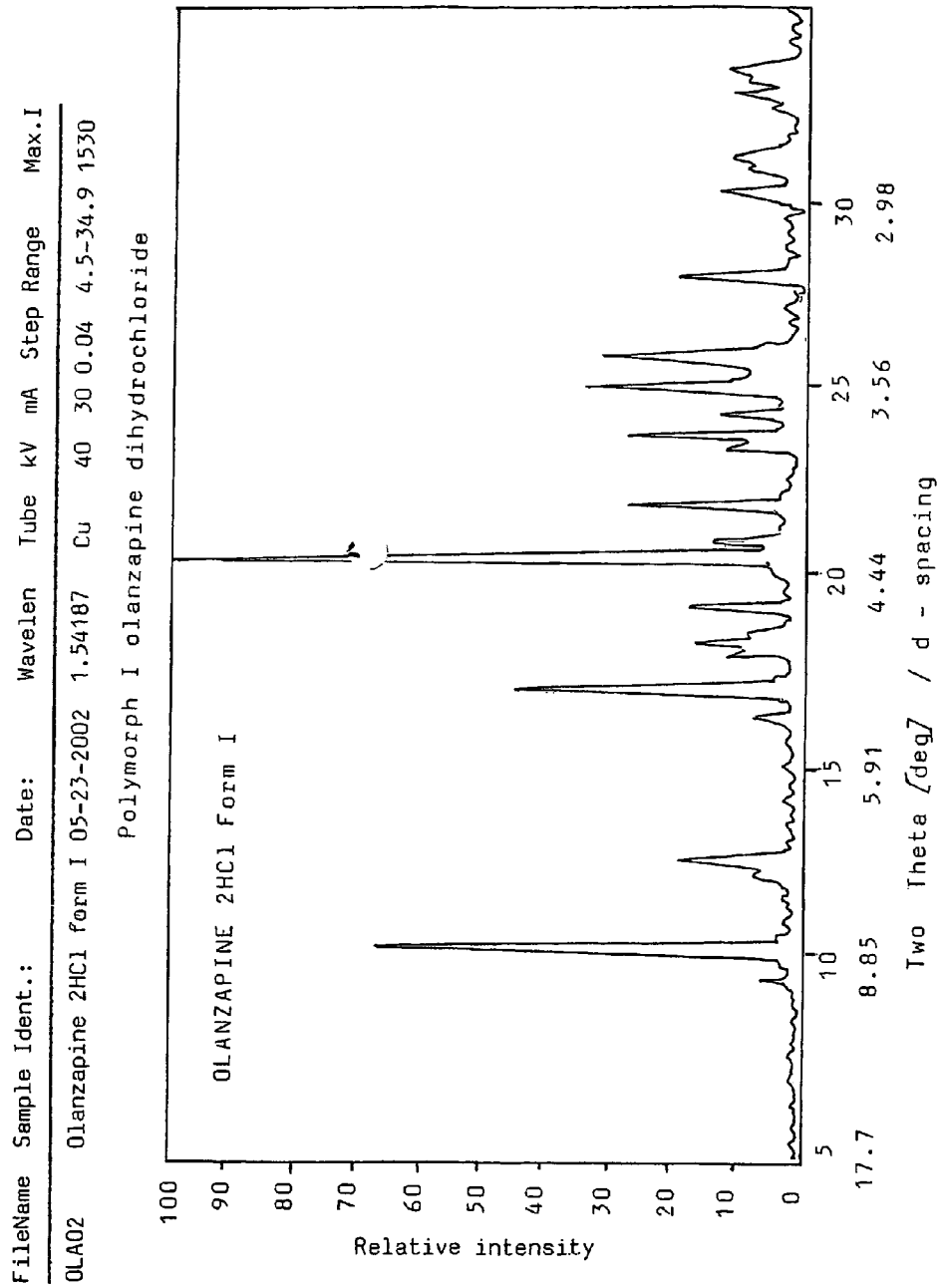
FIG. 1 X-ray powder diffraction pattern of Crystalline form I 2-methyl-4-(4-methyl-piperazin-1-yl)-10H-thieno[2,3-b][1,5]-benzodiazepine dihydrochloride.

According to an aspect of the present invention there is provided new crystalline form I 2-methyl-4-(4-methyl-piperazin-1-yl)-10H-thieno[2,3-b][1,5]-benzodiazepine dihydrochloride characterized by the X-ray powder diffraction pattern expressed in Table 1 and FIG. 1, measured using CuK$_\alpha$ radiation:

TABLE 1

Position of diffraction lines and relative intensities (>5%)

| Peak No. | 2*th [degree] | D(hkl) [Å] | I(abs) [cts] | I(rel) [%] |
|---|---|---|---|---|
| 1 | 10.38 | 8.5918 | 1017 | 66.47 |
| 2 | 12.28 | 7.2072 | 89 | 5.82 |
| 3 | 12.59 | 7.0305 | 303 | 19.80 |
| 4 | 16.31 | 5.4338 | 108 | 7.06 |
| 5 | 17.13 | 5.1770 | 693 | 45.29 |
| 6 | 18.21 | 4.8707 | 158 | 10.33 |
| 7 | 18.40 | 4.8219 | 240 | 15.69 |
| 8 | 19.38 | 4.5802 | 264 | 17.25 |
| 9 | 20.62 | 4.3079 | 1530 | 100 |
| 10 | 21.07 | 4.2157 | 199 | 13.01 |
| 11 | 22.05 | 4.0320 | 424 | 27.71 |
| 12 | 23.50 | 3.7862 | 170 | 11.11 |
| 13 | 23.85 | 3.7314 | 432 | 28.24 |
| 14 | 24.39 | 3.6494 | 142 | 9.28 |
| 15 | 25.10 | 3.5474 | 518 | 33.86 |
| 16 | 25.88 | 3.4434 | 547 | 35.75 |
| 17 | 28.06 | 3.1805 | 309 | 20.20 |
| 18 | 30.26 | 2.9536 | 199 | 13.01 |
| 19 | 30.80 | 2.9028 | 115 | 7.52 |
| 20 | 31.05 | 2.8803 | 152 | 9.93 |
| 21 | 31.17 | 2.8695 | 163 | 10.65 |
| 22 | 32.77 | 2.7328 | 148 | 9.67 |
| 23 | 33.17 | 2.7009 | 136 | 8.89 |
| 24 | 33.31 | 2.6895 | 154 | 10.07 |

The powder diffraction pattern of new crystalline form I 2-methyl-4-(4-methylpiperazin-1-yl)-10H-thieno[2,3-b][1,5]-benzodiazepine dihydrochloride was determined under the following conditions:
Equipment: PHILIPS-XPERT PW 3710 powder diffractometer
Radiation: CuKα (λ: 1.54190 Å)
Monochromator: graphite
Excitation voltage: 40 kV
Anode current: 30 mA
Method:
Standard reference substance: SRM 675 Mica powder (synthetic fluorophlogopite), serial number: 981307
The measurement was continuous: Θ/2Θ
scan: 4.5-35.00° 2Θ
Step size: 0.02-0.04°
Sample: surface plain, width 0.5 mm, in quartz sample holder, measured and stored at room temperature.

According to a further aspect of the present invention there is provided a process for preparation of crystalline form I 2-methyl-4-(4-methylpiperazin-1-yl)-10H-thieno-[2,3-b][1,5]-benzodiazepine dihydrochloride, which comprises a. dissolving 2-methyl-4-(4-methylpiperazin-1-yl)-10H-thieno[2,3-b]-[1,5]-benzodiazepine base in a dipolar aprotic or less polar aprotic or protic solvent or in a mixture of such solvents, reacting the solution with a solution of a dipolar aprotic or less polar aprotic or polar solvent or a mixture of such solvents saturated with gaseous hydrogen chloride and isolating the separated crystalline polymorph, or b. recrystallizing polymorph form II 2-methyl-4-(4-methylpiperazin-1-yl)-10H-thieno[2,3-b][1,5]-benzodiazepine dihydrochloride or a mixture of polymorph forms I and II from a protic solvent, or c. stirring crystalline form II 2-methyl-4-(4-methylpiperazin-1-yl)-10H-thieno[2,3-b][1,5]-benzodiazepine dihydrochloride or a mixture of polymorphs I and II in a protic solvent at about room temperature and isolating the crystalline polymorph.

As dipolar aprotic solvent a ketone, preferably acetone or acetonitrile, an ester, preferably ethyl acetate or a dialkyl amide, preferably dimethyl formamide or a mixture of said solvents can be used.

Particularly advantageous solvents are acetonitrile, acetone or ethyl acetate.

As less polar aprotic solvent ethers, preferably diethyl ether, dioxane, tetrahydrofuran, diisopropyl ether or a mixture thereof can be used. It is particularly preferable to use tetrahydrofuran.

As protic solvent lower alcohols, preferably methanol, ethanol, propanol or 2-propanol, particularly 2-propanol can be used.

Process variant a) can be performed preferably in the following manner: 2-methyl-4-(4-methylpiperazin-1-yl)-10H-thieno[2,3-b][1,5]-benzodiazepine base is dissolved in a dipolar aprotic or less polar aprotic or protic solvent or in a mixture of such solvents under heating, preferably by boiling the reaction mixture using a reflux condenser. Then a solution of a dipolar aprotic or less polar aprotic or polar solvent or a mixture of such solvents saturated by gaseous hydrogen chloride is added to the solution, the reaction mixture is cooled and the precipitating polymorph is isolated. Isolation is preferably carried out by filtration or centrifugation. In order to facilitate the precipitation of the polymorph the solution can be seeded with polymorph form I. It is preferable to carry out the formation of 2-methyl-4-(4-methylpiperazin-1-yl)-10H-thieno[2,3-b][1,5]-benzodiazepine dihydrochloride under heating, preferably by boiling the reaction mixture by using a reflux condenser. The desired polymorph I is obtained upon cooling.

According to process variant b) crystalline form II 2-methyl-4-(4-methylpiperazin-1-yl)-10H-thieno[2,3-b][1,5]-benzodiazepine dihydrochloride or a mixture of polymorph forms I and II is recrystallized from a protic solvent. Crystalline form II 2-methyl-4-(4-methylpiperazin-1-yl)-10H- thieno[2,3-b]-[1,5]-benzodiazepine dihydrochloride can be used in morphologically pure form or as a mixture formed with polymorph form I 2-methyl-4-(4-methylpiperazin-1-yl)-10H-thieno[2,3-b][1,5]-benzodiazepine dihydrochloride. One can proceed by heating—or preferably boiling—the solution, if necessary, filtering off the insoluble contamination and cooling the solution or the filtrate to room temperature. The thus-obtained polymorph form I 2-methyl-4-(4-methylpiperazin-1-yl)-10H-thieno-[2,3-b][1,5]-benzodiazepine dihydrochloride is stirred for 0.1-12 hours and then isolated, preferably by filtration or centrifugation. Crystallization can be enhanced by inoculating the solution with polymorph form I. It is preferable to cool the mixture to a temperature between −20° C. and +15° C., preferably between 0° C. and +15° C., stir it for 0.1-12 hours and isolate the crystals.

According to process variant c) polymorph form II 2-methyl-4-(4-methylpiperazin-1-yl)-10H-thieno[2,3-b][1,5]-benzodiazepine dihydrochloride or a mixture of polymorph forms I and II is stirred in a protic solvent at about room temperature, preferably between 20° C. and 24° C., and the precipitating crystalline polymorph is isolated by filtration or centrifugation. Stirring is carried our preferably for 0.1-12 hours.

Figure 2:
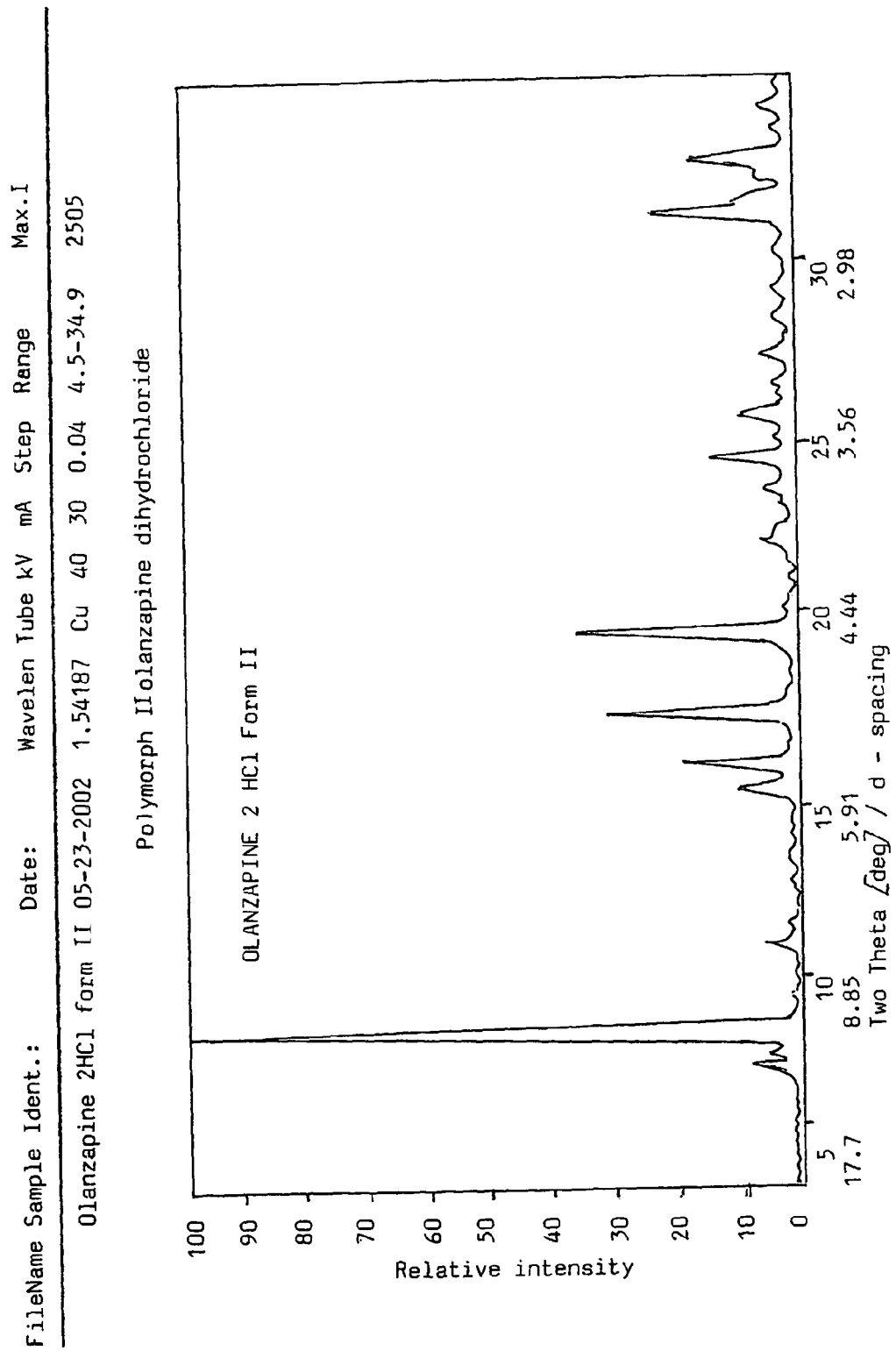
FIG. 2 X-ray powder diffraction pattern of Crystalline form II 2-methyl-4-(4-methyl-piperazin-1-yl)-10H-thieno[2,3-b][1,5]-benzodiazepine dihydrochloride.

According to a further aspect of the present invention there is provided polymorph form II 2-methyl-4-(4-methylpiperazin-1-yl)-10H-thieno[2,3-b]-[1,5]-benzodiazepine dihydrochloride characterized by the X-ray diffraction pattern as set forth in Table 2 and FIG. 2 measured using CuK$_\alpha$ radiation.

TABLE 2

Position of diffraction lines and relative intensities (>5%)

| Peak No. | 2*th [degree] | D(hkl) [Å] | I(abs) [cts] | I(rel) [%] |
|---|---|---|---|---|
| 1 | 7.78 | 11.3638 | 219 | 8.74 |
| 2 | 8.17 | 10.8222 | 124 | 4.95 |
| 3 | 8.79 | 10.0557 | 2505 | 100 |
| 4 | 11.26 | 7.8611 | 143 | 5.71 |
| 5 | 15.54 | 5.7012 | 265 | 10.58 |
| 6 | 16.28 | 5.4444 | 478 | 19.08 |
| 7 | 17.55 | 5.0524 | 817 | 32.61 |
| 8 | 19.78 | 4.4885 | 933 | 37.25 |
| 9 | 22.26 | 3.9945 | 153 | 6.11 |
| 10 | 24.51 | 3.6315 | 348 | 13.89 |
| 11 | 25.75 | 3.4605 | 202 | 8.06 |
| 12 | 25.93 | 3.4362 | 131 | 5.23 |
| 13 | 31.30 | 2.8580 | 558 | 22.28 |
| 14 | 31.53 | 2.8375 | 202 | 8.06 |
| 15 | 32.38 | 2.7651 | 145 | 5.79 |
| 16 | 32.74 | 2.7355 | 404 | 16.13 |

The powder diffraction pattern was determined under the conditions described in connection with polymorph form I.

According to a still further aspect of the present invention there is provided a process for the preparation of crystalline form II 2-methyl-4-(4-methyl-piperazin-1-yl)-10H-thieno[2,3-b]-[1,5]-benzodiazepine dihydrochloride, which comprises subjecting crystalline form I 2-methyl-4-(4-methylpiperazin-1-yl)-10H-thieno[2,3-b][1,5]-benzodiazepine dihydrochloride to recrystallization from a mixture thereof formed with a dipolar aprotic or protic solvent and water.

As dipolar aprotic solvent a ketone, preferably acetone or acetonitrile can be used.

As protic solvent lower aliphatic alcohols, preferably ethanol or isopropanol can be applied.

The mixture consisting of a dipolar aprotic or protic solvent and water contains an amount of 5-100 v/v %, preferably an amount of 10-50 v/v % of water. It is particularly preferable to carry out the reaction by using a mixture of acetone and water, acetonitrile and water, ethanol and water or 2-propanol and water containing 10-20 v/v % of water.

The reaction is preferably carried out in the following manner: crystalline form I 2-methyl-4-(4-methylpiperazin-1-yl)-10H-thieno[2,3-b][1,5]-benzodiazepine dihydrochloride is dissolved in a dipolar aprotic or protic solvent under heating—preferably under boiling—while adding some water to the solution. If necessary, the insoluble contamination is filtered off—optionally while the solution is hot—, the mixture is cooled to about room temperature and stirred for 0.1-1 hour. Crystallization can be facilitated by seeding with crystalline form II polymorph. The separating crystalline form II 2-methyl-4-(4-methylpiperazin-1-yl)-10H-thieno[2,3-b][1,5]-benzodiazepine dihydrochloride is isolated, preferably by filtration or centrifugation.

Figure 3:
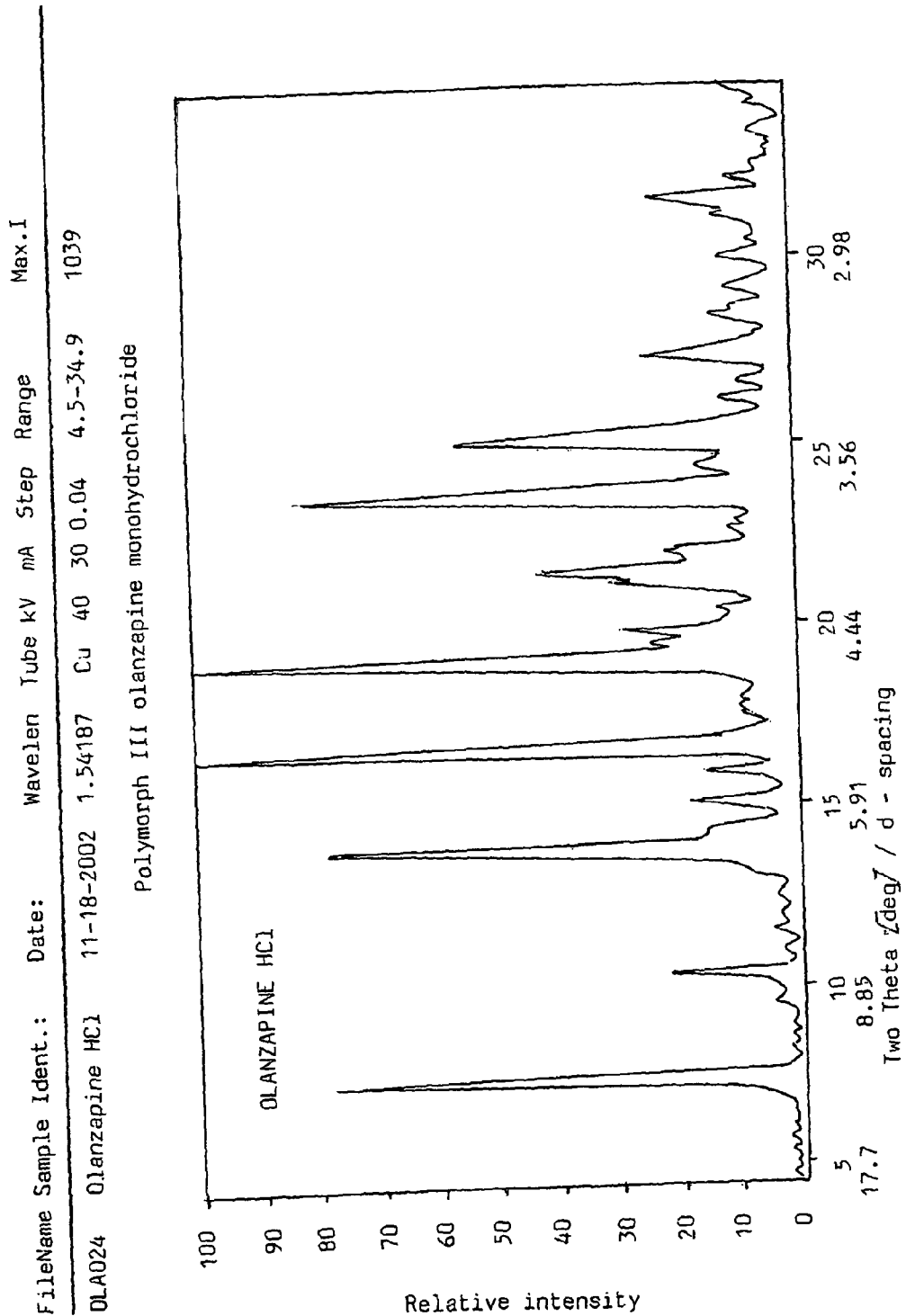
FIG. 3 X-ray powder diffraction pattern of Crystalline form III 2-methyl-4-(4-methyl-piperazin-1-yl)-10H-thieno[2,3-b][1,5]-benzodiazepine monohydrochloride.

According to a further aspect of the present invention there is provided crystalline form III 2-methyl-4-(4-methylpiperazin-1-yl)-10H-thieno[2,3-b]-[1,5]-benzodiazepine monohydrochloride characterized by the X-ray powder diffraction pattern expressed in Table 3 and FIG. 3, measured using CuK$_\alpha$ radiation.

TABLE 3

Position of diffraction lines and relative intensities (>10%)

| Peak Number | 2*th [degrees] | D(hkl) [Å] | I(abs) [cts] | I(rel) [%] |
|---|---|---|---|---|
| 1 | 7.53 | 11.7415 | 806 | 77.58 |
| 2 | 10.41 | 8.4980 | 228 | 21.95 |
| 3 | 13.93 | 6.3575 | 798 | 76.79 |
| 4 | 14.29 | 6.1982 | 147 | 14.15 |
| 5 | 15.12 | 5.8598 | 178 | 17.14 |
| 6 | 15.93 | 5.5629 | 165 | 15.91 |
| 7 | 16.62 | 5.3336 | 1039 | 100 |
| 8 | 19.10 | 4.6474 | 1027 | 98.85 |
| 9 | 19.57 | 4.5362 | 235 | 22.66 |
| 10 | 19.89 | 4.4639 | 299 | 28.75 |
| 11 | 20.53 | 4.3262 | 125 | 11.99 |
| 12 | 21.30 | 4.1721 | 309 | 29.70 |
| 13 | 21.49 | 4.1351 | 439 | 42.29 |
| 14 | 22.09 | 4.0241 | 215 | 20.64 |
| 15 | 23.61 | 3.7679 | 855 | 82.30 |
| 16 | 24.45 | 3.6408 | 154 | 14.87 |
| 17 | 25.21 | 3.5327 | 581 | 55.90 |
| 18 | 26.33 | 3.3849 | 104 | 10.00 |
| 19 | 27.46 | 3.2486 | 259 | 24.90 |
| 20 | 28.56 | 3.1260 | 138 | 13.23 |
| 21 | 29.40 | 3.0376 | 117 | 11.24 |
| 22 | 30.25 | 2.9546 | 128 | 12.36 |
| 23 | 31.29 | 2.8587 | 116 | 11.13 |
| 24 | 31.65 | 2.8270 | 230 | 22.18 |
| 25 | 32.33 | 2.7691 | 98 | 9.44 |

The powder diffraction pattern of the new crystalline form II was determined under the conditions described in connection with crystalline form I.

According to a still further aspect of the invention there is provided a process for the preparation of crystalline form III 2-methyl-4-(4-methylpiperazin-1-yl)-10H-thieno[2,3-b][1,5]-benzodiazepine monohydrochloride, which comprises dissolving 2-methyl-4-(4-methylpiperazin-1-yl)-10H-thieno[2,3-b][1,5]-benzodiazepine in a dipolar aprotic or less polar aprotic solvent or in a mixture of such solvents, reacting the solution with hydrogen chloride in an amount necessary for the formation of monohydrochloride and isolating the precipitated crystalline polymorph.

As dipolar aprotic or less polar aprotic solvent the solvents mentioned in connection with the preparation of polymorph form I can be used. According to a preferred embodiment acetonitrile can be used.

The process is preferably carried out by dissolving 2-methyl-4-(4-methylpiperazin-1-yl)-10H-thieno[2,3-b]-[1,5]-benzodiazepine base in a dipolar aprotic or less polar aprotic solvent and adding a stoichiometric amount of hydrogen chloride necessary for the formation of monohydrochloride. For this purpose preferably a concentrated aqueous solution of hydrogen chloride is used. Salt formation is carried out under heating, preferably under boiling by using a reflux condenser. The reaction mixture is then cooled and the precipitating crystalline form III polymorph is isolated.

According to a still further aspect of the present invention there is provided a pharmaceutical composition comprising crystalline form I, II or III 2-methyl-4-(4-methylpiperazin-1-yl)-10H-thieno-[2,3-b][1,5]-benzodiazepine hydrochloride as active ingredient in admixture with inert, solid or liquid pharmaceutical carriers and/or auxiliary agents and bringing the mixture to galenic form.

The pharmaceutical compositions according to the invention can be prepared by methods conventionally applied in pharmaceutical industry. The pharmaceutical compositions according to the invention can be administered orally (e.g. tablets, coated tablets, capsules, pilules, solutions, suspensions or emulsions), rectally (e.g. suppositories), parenterally (e.g. intravenously, intraperitoneally, etc.) or transdermally.

The pharmaceutical compositions according to the invention may contain usual pharmaceutical carriers and/or auxiliary agents. As carrier magnesium carbonate, magnesium stearate, talc, sucrose, lactose, pectin, dextrin, starch, gelatine, tragacanth, methyl cellulose, sodium carboxymethyl cellulose, low melting wax, cocoa butter etc. can be used. In case of capsules the carrier is generally the wall of the capsule so that no additional carrier is needed. As oral administration form the lozenge and sachet can also be mentioned. Tablets, powders, capsules, pilules, sachets and lozenges are solid forms particularly suitable for oral administration.

Suppositories may contain low melting waxes (e.g. mixtures of fatty acid triglycerides or cocoa butter) as carrier. Suppositories can be prepared by melting the wax, homogeneously distributing the active ingredient in the melt, pouring the melt homogenous mixture into mould forms of suitable size and form, and allowing the mixture to solidify under cooling.

Tablets can be prepared by admixing the active ingredient with suitable carriers in the appropriate ratio and pressing the mixture into tablets of suitable size and form.

Powders are prepared by admixing the finely powdered active ingredient with finely powdered carriers.

As liquid pharmaceutical compositions optionally sustained release solutions, suspensions and emulsions can be mentioned. Aqueous solutions and aqueous propylene glycol solutions are advantageous. Liquid pharmaceutical compositions suitable for parenteral administration can be preferably prepared in the form of aqueous polyethylene glycol solutions.

Aqueous solutions suitable for oral administration can be produced by dissolving the active ingredient in water and adding suitable colouring, aromatizing, stabilizing agents and thickeners.

Aqueous suspensions suitable for oral administration can be prepared by suspending the active ingredient in water in presence of a viscous substance (e.g. natural or artificial gums, resins, methyl cellulose, sodium carboxymethyl cellulose or other known suspending agents).

Another type of solid pharmaceutical compositions can be converted into liquid compositions immediately before use and administered orally into the organism in liquid form. Solutions, suspensions or emulsions can be mentioned as such liquid forms of administration which contain, in addition to the active ingredient, colouring agents, aromatizing agents, preservatives, buffers, artificial or natural sweeteners, dispersing agents, thickeners, etc.

The pharmaceutical compositions of the present invention are preferably prepared in dosage unit form. Such dosage units contain the desired amount of the active ingredient. The dosage units can be put on the market in packages containing discrete amounts of the compositions (e.g. packed tablets, capsules or powders in vials or ampoules). The term "dosage unit" relates to the capsules, tablets, lozenges, sachets per se and also to the packaging which contains the suitable number of dosage units.

The active ingredient may be released from the pharmaceutical compositions according to the present invention immediately or in a delayed manner.

The pharmaceutical compositions according to the present invention usually contain about 0.1-100 mg, preferably about 0.5-50 mg of active ingredient.

According to a still further aspect of the present invention there is provided the use of crystalline form I, II or III 2-methyl-4-(4-methylpiperazin-1-yl)-10H-thieno[2,3-b][1,5]-benzodiazepine hydrochloride as a pharmaceutically active ingredient.

According to a still further aspect of the present invention there is provided the use of crystalline form I, II or III 2-methyl-4-(4-methylpiperazin-1-yl)-10H-thieno[2,3-b][1,5]-benzodiazepine hydrochloride for the preparation of pharmaceutical compositions possessing antipsychotic activity.

According to a still further aspect of the present invention there is provided a method for the treatment of psychotic conditions, which comprises administering to a patient in need of such treatment a pharmaceutically active amount of crystalline form I or II 2-methyl-4-(4-methylpiperazin-1-yl)-10H-thieno[2,3-b][1,5]-benzodiazepine dihydrochloride or crystalline form III 2-methyl-4-(4-methylpiperazin-1-yl)-10H-thieno[2,3-b][1,5]-benzodiazepine monohydrochloride.

Further details of the present invention are provided in the following examples without limiting the scope of protection to said examples.

EXAMPLE 1

Preparation of polymorph form I 2-methyl-4-(4-methylpiperazin-1-yl)-10H-thieno[2,3-b][1,5]-benzodiazepine dihydrochloride 1 g (3.2 mmoles) of olanzapine base is dissolved in 20 cm$^3$ of 1,4-dioxane by boiling in an apparatus equipped with a reflux condenser. Subsequently 3.4 g of hydrogen chloride solution in 1,4-dioxane (34.5 m/m %) are dropped to it. The mixture is cooled in ice-water for 10 minutes and the precipitated yellow product is filtered off. Thus 1.20 g (97%) of the title compound is obtained.

EXAMPLE 2

Preparation of polymorph form I 2-methyl-4-(4-methylpiperazin-1-yl)-10H-thieno[2,3-b][1,5]-benzodiazepine dihydrochloride 1 g (3.2 mmoles) of olanzapine base is dissolved in 20 cm$^3$ of acetonitrile by boiling in an apparatus equipped with a reflux condenser. Subsequently 3.4 g of hydrogen chloride solution in 1,4-dioxane (34.5 m/m %) are dropped to it. The mixture is cooled in ice-water for 10 minutes and the precipitated yellow product is filtered off. Thus 1.20 g (97%) of the title compound is obtained.

EXAMPLE 3

Preparation of polymorph form I 2-methyl-4-(4-methylpiperazin-1-yl)-10H-thieno[2,3-b][1,5]-benzodiazepine dihydrochloride 1 g (3.2 mmoles) of olanzapine base is dissolved in 20 cm$^3$ of tetrahydrofuran by boiling in an apparatus equipped with a reflux condenser. Subsequently 3.4 g of hydrogen chloride solution in 1,4-dioxane (34.5 m/m %) are dropped to it. The mixture is cooled in ice-water for 10 minutes and the precipitated yellow product is filtered off. Thus 1.20 g (97%) of the title compound is obtained.

EXAMPLE 4

Preparation of polymorph form I of 2-methyl-4-(4-methylpiperazin-1-yl)-10H-thieno[2,3-b][1,5]-benzodiazepine dihydrochloride 1 g (3.2 mmoles) of olanzapine base is dissolved in 80 cm$^3$ of 2-propanol by boiling in an apparatus equipped with a reflux condenser. Subsequently 3.7 g of hydrogen chloride solution in 2-propanol (31.5 m/m %) are dropped to it. The mixture is cooled in ice-water for 10 minutes and the precipitated yellow product is filtered off. Thus 1.20 g (97%) of the title compound is obtained.

EXAMPLE 5

Preparation of polymorph form I 2-methyl-4-(4-methylpiperazin-1-yl)-10H-thieno[2,3-b][1,5]-benzodiazepine dihydrochloride 1 g (3.2 mmoles) of olanzapine base is dissolved in 25 cm$^3$ of ethyl acetate by boiling in an apparatus equipped with a reflux condenser. Subsequently 8.5 cm$^3$ of hydrogen chloride solution in ethyl acetate (13.7 g of hydrogen chloride in 100 cm$^3$ of ethyl acetate) are dropped to it. The mixture is cooled in ice-water for 10 minutes and the yellow precipitated product is filtered off. Thus 1.20 g (97%) of the title compound is obtained.

EXAMPLE 6

Preparation of polymorph form II 2-methyl-4-(4-methylpiperazin-1-yl)-10H-thieno[2,3-b][1,5]-benzodiazepine dihydrochloride In an apparatus equipped with a reflux condenser 1 g (2.6 mmoles) of polymorph form I olanzapine dihydrochloride is dissolved in 30 cm$^3$ of boiling acetone while dropping 6 cm$^3$ of water to it. The hot solution is filtered and the filtrate is cooled in an ice-water bath. The precipitated yellow crystals are stirred for 30 minutes, filtered off and dried. Thus 0.8 g (80%) of the title compound is obtained.

EXAMPLE 7

Preparation of polymorph form II 2-methyl-4-(4-methylpiperazin-1-yl)-10H-thieno[2,3-b][1,5]-benzodiazepine dihydrochloride In an apparatus equipped with a reflux condenser 1 g (2.6 mmoles) of polymorph form I olanzapine dihydrochloride is dissolved in 30 cm$^3$ of boiling acetonitrile while dropping 5.6 cm$^3$ of water to the solution. The hot solution is filtered and the filtrate is cooled in an ice-water bath. The precipitated yellow crystals are stirred for 30 minutes, filtered off and dried. Thus 0.8 g (80%) of the title compound is obtained.

EXAMPLE 8

Preparation of polymorph form II 2-methyl-4-(4-methylpiperazin-1-yl)-10H-thieno[2,3-b][1,5]-benzodiazepine dihydrochloride In an apparatus equipped with a reflux condenser 1 g (2.6 mmoles) of polymorph form I olanzapine dihydrochloride is dissolved in 30 cm$^3$ of boiling 2-propanol while dropping 4.6 cm$^3$ of water to the solution. The hot solution is filtered and the filtrate is cooled in an ice-water bath. The precipitated yellow crystals are stirred for 30 minutes, filtered off and dried. Thus 0.8 g (80%) of the title compound is obtained.

EXAMPLE 9

Preparation of polymorph form II 2-methyl-4-(4-methylpiperazin-1-yl)-10H-thieno[2,3-b][1,5]-benzodiazepine dihydrochloride In an apparatus equipped with a reflux condenser 1 g (2.6 mmoles) of polymorph form I olanzapine dihydrochloride is dissolved in 15 cm$^3$ of boiling ethanol while dropping 1.6 cm$^3$ of water to the solution. The hot solution is filtered and the filtrate is cooled using ice-water bath. The precipitated yellow crystals are stirred for 60 minutes, filtered off and dried. Thus 0.8 g (80%) of the title compound is obtained.

EXAMPLE 10

Preparation of polymorph form I 2-methyl-4-(4-methylpiperazin-1-yl)-10H-thieno[2,3-b][1,5]-benzodiazepine dihydrochloride 1 g (2.6 mmoles) of polymorph form II olanzapine dihydrochloride is stirred vigorously in 10 cm$^3$ of ethanol for 30 minutes at room temperature. The yellow crystals are then filtered off and dried. Thus 0.93 g (93%) of the title compound is obtained.

EXAMPLE 11

Preparation of polymorph form I 2-methyl-4-(4-methylpiperazin-1-yl)-10H-thieno[2,3-b][1,5]-benzodiazepine dihydrochloride 1 g (2.6 mmoles) of polymorph form II olanzapine dihydrochloride is stirred vigorously in 5 cm$^3$ of methanol for 30 minutes at room temperature. The yellow crystals are then filtered and dried. Thus 0.9 g (90%) of the title compound is obtained.

EXAMPLE 12

Preparation of polymorph form I 2-methyl-4-(4-methylpiperazin-1-yl)-10H-thieno[2,3-b][1,5]-benzodiazepine dihydrochloride In an apparatus equipped with a reflux condenser 1 g (2.6 mmoles) of polymorph form II olanzapine dihydrochloride is dissolved in 17.5 cm³ of boiling methanol. The hot solution is filtered and the filtrate is cooled in an ice-water bath. The yellow crystals are stirred for 3 hours, filtered off and dried. Thus 0.6 g (60%) of the title compound is obtained.

EXAMPLE 13

Preparation of polymorph form III 2-methyl-4-(4-methylpiperazin-1-yl)-10H-thieno[2,3-b][1,5]-benzodiazepine monohydrochloride In an apparatus equipped with a reflux condenser 1 g (3.2 mmoles) of olanzapine base is dissolved in 20 cm³ of acetonitrile by heating until boiling. Subsequently 3.2 g of concentrated aqueous hydrochloric acid solution are dropped to it (37.0 g of hydrogen chloride in 100 cm³ of water). The reaction mixture is cooled for 10 minutes in an ice-water bath and the yellow precipitate is filtered off. Thus 1.1 g (98.5%) of the title compound is obtained.

EXAMPLE 14

Preparation of polymorph form II 2-methyl-4-(4-methylpiperazin-1-yl)-10H-thieno[2,3-b][1,5]-benzodiazepine dihydrochloride In an apparatus equipped with a reflux condenser 1 g (2.6 mmoles) of polymorph form I olanzapine dihydrochloride is dissolved in 2.7 cm³ of boiling water. The mixture is stirred for 15 minutes, cooled in an ice-water bath and the yellow precipitate is filtered off. Thus 0.8 g (80%) of the title compound is obtained.

What we claim is:

1. Crystalline form I of 2-methyl-4-(4-methylpiperazin-1-yl)-10H-thieno[2,3-b][1,5]-benzodiazepine dihydrochloride, wherein the X-ray powder diffraction data and pattern are shown in Table 1 and FIG. 1, respectively, measured using CuK$_\alpha$ radiation:

TABLE 1

Position of diffraction lines and relative intensities (>5%)

| Peak No. | 2*th [degree] | D(hkl) [Å] | I(abs) [cts] | I(rel) [%] |
|---|---|---|---|---|
| 1 | 10.38 | 8.5918 | 1017 | 66.47 |
| 2 | 12.28 | 7.2072 | 89 | 5.82 |
| 3 | 12.59 | 7.0305 | 303 | 19.80 |
| 4 | 16.31 | 5.4338 | 108 | 7.06 |
| 5 | 17.13 | 5.1770 | 693 | 45.29 |
| 6 | 18.21 | 4.8707 | 158 | 10.33 |
| 7 | 18.40 | 4.8219 | 240 | 15.69 |
| 8 | 19.38 | 4.5802 | 264 | 17.25 |
| 9 | 20.62 | 4.3079 | 1530 | 100 |
| 10 | 21.07 | 4.2157 | 199 | 13.01 |
| 11 | 22.05 | 4.0320 | 424 | 27.71 |
| 12 | 23.50 | 3.7862 | 170 | 11.11 |
| 13 | 23.85 | 3.7314 | 432 | 28.24 |
| 14 | 24.39 | 3.6494 | 142 | 9.28 |
| 15 | 25.10 | 3.5474 | 518 | 33.86 |
| 16 | 25.88 | 3.4434 | 547 | 35.75 |
| 17 | 28.06 | 3.1805 | 309 | 20.20 |
| 18 | 30.26 | 2.9536 | 199 | 13.01 |
| 19 | 30.80 | 2.9028 | 115 | 7.52 |
| 20 | 31.05 | 2.8803 | 152 | 9.93 |
| 21 | 31.17 | 2.8695 | 163 | 10.65 |
| 22 | 32.77 | 2.7328 | 148 | 9.67 |
| 23 | 33.17 | 2.7009 | 136 | 8.89 |
| 24 | 33.31 | 2.6895 | 154 | 10.07. |

2. A process for preparation of crystalline form I of 2-methyl-4-(4-methylpiperazin-1-yl)-10H-thieno[2,3-b][1,5]-benzodiazepine dihydrochloride, said process comprising:
   a) dissolving 2-methyl-4-(4-methyl-piperazin-1-yl)-10H-thieno [2,3-b][1,5]-benzodiazepine base in a dipolar aprotic or less polar aprotic or protic solvent or in a mixture of such solvents, reacting the solution with a solution of a dipolar aprotic or less polar aprotic or polar solvent or a mixture of such solvents saturated with gaseous hydrogen chloride and isolating the separated crystalline polymorph, or
   b) recrystallizing polymorph form II of 2-methyl-4-(4-methylpiperazin-1-yl)-10H-thieno[2,3-b][1,5]-benzodiazepine dihydrochloride or a mixture of polymorph forms I and II from a protic solvent, or
   c) stirring polymorph form II of 2-methyl-4-(4-methylpiperazin-1-yl)-10H-thieno [2,3-b][1,5]-benzodiazepine dihydrochloride or a mixture of polymorph forms I and II in a protic solvent at about room temperature and isolating the crystalline polymorph.

3. The process according to claim 2, which comprises using a dipolar aprotic solvent, said solvent being a ketone, an ester, a dialkyl amide, or a mixture thereof.

4. The process according to claim 2, which comprises using a less polar aprotic solvent, said less polar aprotic solvent being an ether.

5. The process according to claim 2, which comprises using a protic solvent of a lower aliphatic alcohol.

6. A method for antipsychotic treatment, which comprises administering to the patient in need of such treatment a pharmaceutically efficient amount of crystalline form I of 2-methyl-4-(4-methylpiperazin-1-yl)-10H-thieno[2,3-b][1,5]-benzodiazepine dihydrochloride.

7. Crystalline form II of 2-methyl-4-(4-methylpiperazin-1-yl)-10H-thieno[2,3-b][1,5]-benzodiazepine dihydrochloride, wherein the X-ray powder diffraction data and pattern are shown in Table 2 and FIG. 2, respectively, measured using CuK$_\alpha$ radiation:

TABLE 2

Position of diffraction lines and relative intensities (>5%)

| Peak Number | 2*th [degree] | D(hkl) [Å] | I(abs) [cts] | I(rel) [%] |
|---|---|---|---|---|
| 1 | 7.78 | 11.3638 | 219 | 8.74 |
| 2 | 8.17 | 10.8222 | 124 | 4.95 |
| 3 | 8.79 | 10.0557 | 2505 | 100 |
| 4 | 11.26 | 7.8611 | 143 | 5.71 |
| 5 | 15.54 | 5.7012 | 265 | 10.58 |
| 6 | 16.28 | 5.4444 | 478 | 19.08 |

TABLE 2-continued

Position of diffraction lines and
relative intensities (>5%)

| Peak Number | 2*th [degree] | D(hkl) [Å] | I(abs) [cts] | I(rel) [%] |
|---|---|---|---|---|
| 7 | 17.55 | 5.0524 | 817 | 32.61 |
| 8 | 19.78 | 4.4885 | 933 | 37.25 |
| 9 | 22.26 | 3.9945 | 153 | 6.11 |
| 10 | 24.51 | 3.6315 | 348 | 13.89 |
| 11 | 25.75 | 3.4605 | 202 | 8.06 |
| 12 | 25.93 | 3.4362 | 131 | 5.23 |
| 13 | 31.30 | 2.8580 | 558 | 22.28 |
| 14 | 31.53 | 2.8375 | 202 | 8.06 |
| 15 | 32.38 | 2.7651 | 145 | 5.79 |
| 16 | 32.74 | 2.7355 | 404 | 16.13. |

8. A process for the preparation of crystalline form II of 2-methyl-4-(4-methylpiperazin-1-yl)-10H-thieno[2,3-b][1,5]-benzodiazepine dihydrochloride, said process comprising:
recrystallizing crystalline form I of 2-methyl-4-(4-methylpiperazin-1-yl)-10H-thieno[2,3-b][1,5]-benzodiazepine dihydrochloride from a mixture of a dipolar aprotic or protic solvent formed with water.

9. The process according to claim 8, which comprises using as ketone a dipolar aprotic solvent.

10. The process according to claim 8, which comprises using a protic solvent of a lower aliphatic alcohol.

11. A method for antipsychotic treatment, which comprises administering to the patient in need of such treatment a pharmaceutically efficient amount of crystalline form II of 2-methyl-4-(4-methylpiperazin-1-yl)-10H-thieno[2,3-b][1,5]-benzodiazepine dihydrochloride.

12. Crystalline form III of 2-methyl-4-(4-methylpiperazin-1-yl)-10H-thieno-[2,3-b][1,5]-benzodiazepine monohydrochloride, wherein the X-ray powder diffraction data and pattern are shown in Table 3 and FIG. 3, respectively, measured using CuK$_\alpha$ radiation:

TABLE 3

Position of diffraction lines and
relative intensities (>5%)

| Peak Number | 2*th [degrees] | D(hkl) [Å] | I(abs) [cts] | I(rel) [%] |
|---|---|---|---|---|
| 1 | 7.53 | 11.7415 | 806 | 77.58 |
| 2 | 10.41 | 8.4980 | 228 | 21.95 |
| 3 | 13.93 | 6.3575 | 798 | 76.79 |
| 4 | 14.29 | 6.1982 | 147 | 14.15 |
| 5 | 15.12 | 5.8598 | 178 | 17.14 |
| 6 | 15.93 | 5.5629 | 165 | 15.91 |
| 7 | 16.62 | 5.3336 | 1039 | 100 |
| 8 | 19.10 | 4.6474 | 1027 | 98.85 |
| 9 | 19.57 | 4.5362 | 235 | 22.66 |
| 10 | 19.89 | 4.4639 | 299 | 28.75 |
| 11 | 20.53 | 4.3262 | 125 | 11.99 |
| 12 | 21.30 | 4.1721 | 309 | 29.70 |
| 13 | 21.49 | 4.1351 | 439 | 42.29 |
| 14 | 22.09 | 4.0241 | 215 | 20.64 |
| 15 | 23.61 | 3.7679 | 855 | 82.30 |
| 16 | 24.45 | 3.6408 | 154 | 14.87 |
| 17 | 25.21 | 3.5327 | 581 | 55.90 |
| 18 | 26.33 | 3.3849 | 104 | 10.00 |
| 19 | 27.46 | 3.2486 | 259 | 24.90 |
| 20 | 28.56 | 3.1260 | 138 | 13.23 |
| 21 | 29.40 | 3.0376 | 117 | 11.24 |
| 22 | 30.25 | 2.9546 | 128 | 12.36 |
| 23 | 31.29 | 2.8587 | 116 | 11.13 |
| 24 | 31.65 | 2.8270 | 230 | 22.18 |
| 25 | 32.33 | 2.7691 | 98 | 9.44. |

13. A process for the preparation of crystalline form III of 2-methyl-4-(4-methylpiperazin-1-yl)-10H-thieno[2,3-b][1,5]-benzodiazepine monohydrochloride, which comprises:
dissolving 2-methyl-4-(4-methylpiperazin-1-yl)-10H-thieno[2,3-b][1,5]-benzodiazepine base in a dipolar aprotic or less polar aprotic solvent or mixture of such solvents,
reacting said solution with an amount of hydrogen chloride necessary for the formation of monohydrochloride, and
isolating the separated crystalline polymorph.

14. The process according to claim 13, which comprises using the dipolar aprotic solvent, said solvent being acetonitrile, a ketone, an ester, a dialkyl amide, or a mixture thereof.

15. A method for antipsychotic treatment, which comprises administering to the patient in need of such treatment a pharmaceutically efficient amount of crystalline form III of 2-methyl-4-(4-methylpiperazin-1-yl)-10H-thieno[2,3-b][1,5]-benzodiazepine monohydrochloride.

16. The process according to claim 2, wherein said dipolar aprotic solvent is selected from the group consisting of acetone, acetonitrile, ethyl acetate, dimethyl formamide and a mixture thereof.

17. The process according to claim 2, wherein said less polar aprotic solvent is selected from the group consisting of diethyl ether, dioxane, tetrahydrofuran, diisopropyl ether and a mixture thereof.

18. The process according to claim 2, wherein said protic solvent is selected from the group consisting of methanol, ethanol, propanol and 2-propanol.

19. The process according to claim 8, wherein said dipolar aprotic solvent is acetone or acetonitrile.

20. The process according to claim 8, wherein said protic solvent is ethanol or isopropanol.

21. The process according to claim 13, wherein said dipolar aprotic solvent is selected from the group consisting of acetone, ethyl acetate, dimethyl formamide and a mixture thereof.

* * * * *